(12) United States Patent
Fahl

(10) Patent No.: US 10,881,824 B2
(45) Date of Patent: Jan. 5, 2021

(54) TRACHEOSTOMA PROTECTION

(71) Applicant: Andreas Fahl Medizintechnik—Vertrieb GmbH, Cologne (DE)

(72) Inventor: Andreas Fahl, Cologne (DE)

(73) Assignee: Andreas Fahl Medizintechnik—Vertrieb GmbH, Cologne (DE)

(*) Notice: Subject to any disclaimer, the term of this patent is extended or adjusted under 35 U.S.C. 154(b) by 733 days.

(21) Appl. No.: 15/537,008

(22) PCT Filed: Dec. 18, 2015

(86) PCT No.: PCT/EP2015/080678
§ 371 (c)(1),
(2) Date: Jun. 16, 2017

(87) PCT Pub. No.: WO2016/097383
PCT Pub. Date: Jun. 23, 2016

(65) Prior Publication Data
US 2018/0028771 A1     Feb. 1, 2018

(30) Foreign Application Priority Data

Dec. 18, 2014 (DE) .................... 10 2014 018 678

(51) Int. Cl.
*A61M 16/04* (2006.01)
*A61F 13/12* (2006.01)
(Continued)

(52) U.S. Cl.
CPC ......... *A61M 16/047* (2013.01); *A61F 13/128* (2013.01); *A61F 2013/530802* (2013.01);
(Continued)

(58) Field of Classification Search
CPC .......... A61M 16/047; A61M 2205/582; A61F 13/128; A61F 2013/530802; A61F 2013/5672; A61F 2013/5677
See application file for complete search history.

(56) References Cited

U.S. PATENT DOCUMENTS

| 2005/0066816 | A1 | 3/2005 | Wright |
| 2009/0227972 | A1 | 9/2009 | Pino Aragones et al. |
| 2010/0288284 | A1* | 11/2010 | Persson ............. A61M 16/0468 128/207.14 |

FOREIGN PATENT DOCUMENTS

| CN | 204158851 U * | 2/2015 |
| DE | 20119493 U1 | 3/2002 |

(Continued)

OTHER PUBLICATIONS

International Search Report dated Mar. 11, 2016, International Application No. PCT/EP2015/080678, filed Dec. 18, 2015.

*Primary Examiner* — Timothy A Stanis
*Assistant Examiner* — Arielle Wolff
(74) *Attorney, Agent, or Firm* — Dinsmore & Shohl LLP

(57) ABSTRACT

The invention relates to a tracheostoma protection device for covering a tracheostoma, comprising an open-cell foam cloth, an adhesive strip and an air-impermeable region arranged distally on the foam cloth and associated with the tracheostoma, the tracheostoma being concealable by means of the air-impermeable region. During use of the tracheostoma protection, the foam cloth can by moved at least to some degree outwardly from a contact surface about the tracheostoma.

11 Claims, 3 Drawing Sheets

(51) Int. Cl.
*A61F 13/53* (2006.01)
*A61F 13/56* (2006.01)

(52) U.S. Cl.
CPC ......... *A61F 2013/5672* (2013.01); *A61F 2013/5677* (2013.01); *A61M 2205/582* (2013.01)

(56) References Cited

FOREIGN PATENT DOCUMENTS

| | | | | |
|---|---|---|---|---|
| DE | 69817327 T2 | 6/2004 | | |
| DE | 202004010800 U1 * | 9/2004 | ......... | A61M 16/047 |
| DE | 202004010800 U1 | 9/2004 | | |
| DE | 202013010194 U1 | 11/2013 | | |
| EP | 3488888 A1 * | 5/2019 | ......... | A61M 16/047 |

* cited by examiner

US 10,881,824 B2

TRACHEOSTOMA PROTECTION

CROSS-REFERENCE TO RELATED APPLICATIONS

This application is a U.S. National Phase of PCT/EP2015/080678, which claims priority of German Patent Application 102014018678.4 filed on Dec. 18, 2014, the contents of which are herewith incorporated by reference into the subject matter of the present patent application.

FIELD OF THE INVENTION

The invention relates to a tracheostoma protection for covering a tracheostoma, comprising an open-cell foam patch.

BACKGROUND OF THE INVENTION

Devices for protecting a tracheostoma are known in general from the prior art. Thus, DE 698 17 327 T2 describes a respiratory protection shield for patients with a tracheostoma. This comprises a thick moisture-/heat-exchange body made of an open-cell foam, which is attached with adhesive to the throat in the proximity of the tracheostoma, or a tracheostoma rim. The distal surface of the device is provided with a cover plate, which deflects the airflow.

SUMMARY OF THE INVENTION

The disadvantage with the tracheostoma protection known from the prior art is that it is difficult to handle. In particular, the tracheostoma protection described therein is uncomfortable when used with a voice prosthesis. In order to trigger the speech process, the stoma is closed, such that the air is conducted through the speaking valve when exhaling. If, for example, it is closed by compressing the tracheostoma protection known from the prior art, the moisture present in the thick foam is pressed out, and flows into the patient's trachea, or soils his clothing. At the same time, the adhesive becomes detached by the escaping fluid. The attachment of the known tracheostoma protection can also be difficult, because the known tracheostoma protection must be attached to the portion of skin bordering the tracheostoma. Only very small tolerances are allowed for thereby, because a displaced adhesion means that the adhesive portion of the tracheostoma overlaps at least a portion of the stoma, and can obstruct respiration. The designs described in DE 698 17 327 T1 also reduce the effective air intake diameter, or the diameter of the tracheostoma, respectively. Furthermore, the adhesive can cause skin irritation—no matter how gentle it feels—particularly to the highly sensitive skin on the rim of the tracheostoma, or the scar tissue surrounding the tracheostoma.

The object of the invention is to eliminate the disadvantages known from the prior art.

Further advantageous designs can be derived from the dependent Claims, the description, and the drawings. Individual features of the different designs can be combined with one another or with further features.

A tracheostoma protection for covering a tracheostoma is proposed, comprising an open-cell foam patch, an adhesive strip, and an air-impermeable region disposed on the distal surface of the foam patch, and which can be allocated to the tracheostoma. The tracheostoma can be covered by the air-impermeable region. When the tracheostoma protection is used, the foam patch can be moved, at least partially, distally away from a contact surface.

If directions are used in the description of the invention, these are to be understood with respect to the normal use of the tracheostoma protection. Direction designations are used in the normal manner in anatomy. The term "distal," as used in the present invention with respect to a feature of the device according to the invention, means that said feature is disposed or used at a distance to, or facing away from, or lying opposite a tracheostoma or a skin surface of a user, in particular wearing the tracheostoma protection according to the invention. Distal is preferably understood to be a direction away from the body of the patient. The term "proximal," as used in the present invention with respect to a feature of the device according to the invention, means that said feature is disposed or used in the proximity of, or facing toward, or adjacent to a tracheostoma or a skin surface of a user, in particular wearing the tracheostoma protection according to the invention. Proximal is preferably understood to be a direction toward the body of the patient. "Transverse" is preferably understood to mean a lateral direction toward the right and/or left of a median plane, or a median line. "Longitudinal" is preferably understood to mean an upward and/or downward direction along the median plane or a median line, in particular the longitudinal axis of the body. "Superior" is preferably understood to mean a relative direction along or parallel to the longitudinal axis of the body above a reference point. "Inferior" is preferably understood to mean a relative direction along or parallel to the longitudinal axis of the body lying below a reference point.

As set forth in the invention, the contact surface is the part of a patient, in particular a section of the skin, that the tracheostoma protection comes in contact with during inhalation.

The proposed tracheostoma protection is comfortable and can be worn discreetly, and reduces abrasions to the skin of the patient, which are known to occur with the speaking valves known from the prior art. Not least of all, such a tracheostoma protection can be produced easily and inexpensively. Furthermore, the diameter of the tracheostoma is retained, such that the respiration remains nearly undisrupted with the proposed tracheostoma protection.

The tracheostoma protection is preferably attached over the tracheostoma of a patient, preferably such that the air-impermeable region is substantially disposed over the tracheostoma, in particular only on the distal surface of the foam patch.

If the term "approximately" is used in the scope of the invention with respect to values or ranges of values, a tolerance range is to be understood thereby, regarded by the person skilled in the art in this field as typical, in particular a tolerance range of ±20%, preferably ±10% in relation to the given values is provided. The term "substantially" also indicates a tolerance range that is acceptable for the person skilled in the art taking economic and technical perspectives into account, such that said feature can still be recognized as such.

The term "adhesive strip" can also be understood in the scope of the invention to mean adhesive regions and/or adhesive points. In a preferred design, the at least one adhesive strip comprises an adhesive tape having adhesive on both sides. The double-sided adhesive tape is preferably designed as an adhesive ring. A ring, as set forth in the invention, e.g. an adhesive ring, is understood to mean a surface between two line geometries lying in a plane that do not intersect, e.g. a circular ring, a rectangular ring and/or a shield-shaped ring. An outer edge of the ring is preferably designed such that it is approximately identical to an outer edge of a proximal surface of the foam patch. Moreover, an inner edge of the ring is preferably substantially geometrically similar to the outer edge of the ring. By way of example, the outer edge of the proximal surface of the foam patch corresponds to the shape of a shield, having a U-shaped, or semicircular, rounded tip, for example. By way of example, the adhesive strip in the form of an adhesive tape can be a ring likewise having the shape of a shield. The outer edge of the ring approximately resembles the outer edge of the foam patch, or borders this outer edge. The inner edge of the annular adhesive strip is preferably substantially geometrically similar to the outer edge, likewise having the shape of a shield in this example, but having smaller dimensions.

According to one design, the foam patch has a substantially rectangular shape seen from the distal side, from above, preferably with rounded corners. In a further design, the foam patch has a rounded shape, e.g. the shape of a water drop, an elliptical shape, or a circular shape. In another embodiment, the foam patch can have an arbitrary shape, seen from above.

According to one embodiment, it is provided that the adhesive strip is an adhesive applied to the foam. Another embodiment provides that the adhesive strip is an adhesive tape, e.g. comprising a double-sided adhesive tape, applied to the foam patch. The adhesive strip is preferably disposed on the proximal surface of the foam patch. In another embodiment it is provided that the adhesive tape comprises an annular bandage. Advantageously, the adhesive strip ensures that the tracheostoma protection remains attached to the throat of the patient, despite the displacement of the foam patch during exhalation. Furthermore, it is preferably ensured with the different embodiments of the adhesive strip that the foam patch can be moved by the airflow, at least partially, distally away from the tracheostoma, in particular during exhalation.

The advantage with the proposed tracheostoma protection is that a speaking function can be readily implemented through the air-impermeable region, in that a light finger pressure is exerted on this region, and the tracheostoma is closed in this manner. Furthermore, in contrast to the speaking valves known from the prior art, breathing is advantageously not obstructed. Instead, it is easier to exhale, because the foam patch can move, at least in part, distally away from a contact plane. The airflow can also flow past the foam patch in one design. The advantage with the designs described herein is that the airflow, in particular during exhalation, flows in part past the foam patch in one embodiment during exhalation. As a result, there is less resistance during exhalation, which is perceived as uncomfortable, in particular during athletic activities.

It is provided in another design that when the tracheostoma protection is used, an airflow during inhalation flows, in particular from the distal toward the proximal surface, substantially through the foam patch. The foam patch preferably lies on the throat of the patient, or the contact plane, such that the airflow only flows through the foam patch during inhalation. This is particularly advantageous because the tracheostoma needs to be protected from foreign matter specifically during inhalation. It is furthermore advantageous that the airflow is pre-warmed and moistened by the tracheostoma protection, before it arrives in the trachea, i.e. the windpipe.

It is provided in another embodiment that when the tracheostoma protection is used, an airflow during the exhalation flows substantially from the proximal toward the distal surface. This is the case in particular when the foam patch is attached to the contact plane on at least two sides, e.g. by the adhesive strip and/or by an article of clothing. If two or more adhesive strips are provided, these can be disposed longitudinally and/or transverse to the air-impermeable region. The retaining of the foam patch on at least two sides or by an annular bandage, e.g. an annular adhesive strip, has no effect on the distal movement away from the contact plane in one embodiment. Instead, the tracheostoma protection, or the foam patch, respectively, is inflated, which is likewise subsumed in one design through the partial displacement of the foam patch. If the foam patch is partially displaced during exhalation, a portion of the air then flows through the foam patch, such that it becomes moistened and warmed.

The advantage with the designs described herein is that the airflow flows substantially from the proximal toward the distal surface through the foam patch in one embodiment, in particular during exhalation. A lateral or longitudinal outflow of the air, in particular parallel to the skin, from the tracheostoma protection during exhalation is frequently perceived as uncomfortable, because in colder weather in particular, the skin surrounding the tracheostoma, or surrounding the tracheostoma protection, becomes chilled. An outflowing of the air substantially from the proximal toward the distal surface keeps the moist exhalation air away from the surrounding skin. Preferably, the air-impermeable region is disposed such that a flowing around it by exhaled air is ensured. The air guidance is advantageously achieved by means of the lateral and/or longitudinal extension of the tracheostoma protection and/or the thickness of the foam patch. It is furthermore advantageously ensured in one design having a substantially annular adhesive strip, that the skin surrounding the tracheostoma is covered by the targeted inflation of the tracheostoma protection by the exhalation air in conjunction with the foam patch, such that the skin surrounding the stoma remains warm.

Preferably, when using the tracheostoma protection, at least a portion of an airflow flows past the foam patch during exhalation.

It is provided in another design that the foam patch has a transverse or longitudinal diameter that is at least twice as large as a diameter of the air-impermeable region. The advantage with this feature is that the tracheostoma protection is more comfortable to wear than devices from the prior art. In particular, abrasions and skin irritations caused by the materials on the throat are reduced by the large contact surface. Furthermore, it is advantageous that the tracheostoma protection can be easily handled. Thus, it must not be placed precisely over the tracheostoma, but rather, it allows for greater tolerances than with speaking valves known from the prior art, in order to ensure at least a moisture-/heat-exchange function. Another advantage is that the adhesive strip can be placed far enough away from the tracheostoma that the sensitive tissues surrounding the tracheostoma, or the tracheostoma rim, are not irritated by the adhesive or the daily changing of the tracheostoma protection.

It is furthermore advantageous with this design that the moisture can be transported far away from the tracheostoma, preferably by the capillary effect of the foam. With speaking valves known from the prior art, the moisture remains in the proximity of the tracheostoma, such that when the foam of the speaking valve is pressed, this moisture is pressed out, and liquid flows into the trachea or the clothing of the patient.

It is provided in another design that the foam patch has a thickness of approximately 1 mm to approximately 8 mm, preferably approx. 1 mm to approx. 6 mm, more preferably approx. 2 mm to approx. 5 mm. Advantageously, this results in a low structural thickness. As a result, the tracheostoma protection is less conspicuous and is comfortable to wear, because clothing does not readily interact therewith. Furthermore, the tracheostoma protection absorbs less liquid per square centimeter of surface area than the speaking valves known from the prior art. In this manner, an amount of liquid squeezed out of the foam patch when initiating the speaking function is reduced or eliminated. It is furthermore advantageous that a pressure for closing the tracheostoma does not have to be exerted as strongly as with the speaking valves known from the prior art, such that an unpleasant pressure to the tracheostoma rim can be reduced, while retaining functionality.

It is provided in another design that the air-impermeable region comprises a button, a plate and/or a skin of the cloth. Advantageously, the air-impermeable region simplifies a closing of the tracheostoma and gives the patient feedback indicating that he has pressed at the correct location. This can be achieved by a surface design for obtaining a special appearance and/or haptic, or by a greater rigidity in relation to the foam patch. In particular, the button or the plate exhibits good feedback properties. If the impermeable region comprises a button or a plate made of a material that is rigid in comparison to a foam material of the foam patch, this makes it easier for the user to compress the foam material when initiating the speaking function.

It is provided in one embodiment that the button or the plate is glued, welded and/or sewn on. Furthermore, one design provides that the button or the plate is welded on. According to one variation, the foam is sprayed or foamed onto the button or the plate. In one design, in which a skin is provided on the foam patch, the skin is generated by melting and cooling a surface region of the foam patch. It is provided in another design that the skin comprises a film that has been glued or welded on.

It is provided in another embodiment that the air-impermeable region can be moved in the proximal direction during use in order to initiate a speaking function. In particular, it is provided that a foam material is provided proximal to the air-impermeable region, which can be compressed. When the air-impermeable region is moved in the proximal direction, the foam material of the foam patch becomes compressed in the region of the tracheostoma. It is provided in another design that the tracheostoma can be closed by means of the air-impermeable region. In particular, the air-impermeable region can be moved close enough to the tracheostoma that no air can escape from the tracheostoma. Because the foam patch is very thin, in some circumstances the compression may not be sufficient for ensuring a sufficient air-impermeability. It is however ensured by the air-impermeable region that only very little to no air can escape from the tracheostoma when initiating the speech process during the actuation of the tracheostoma protection through finger pressure. At the same time, a comfortable respiration is ensured, due to the distal position of the air-impermeable region.

It is provided in another embodiment that the adhesive strip is disposed on the foam patch such that it can be attached substantially superior to the tracheostoma. The adhesive strip is, in particular, a curved or straight strip. It is provided in one design that a number of adhesive strips, adhesive regions and/or adhesive points are provided on the foam patch. Furthermore, the adhesive strip can also extend at least partially around the tracheostoma, or around the air-impermeable region. It is provided in another design that the adhesive strip extends substantially entirely around the tracheostoma or the air-impermeable region. It is provided in another design that the adhesive strip is disposed in the region of a longitudinal and/or transverse edge of the foam patch. It is provided in another embodiment that the adhesive strip is disposed substantially bordering on a lateral and/or longitudinal edge of the foam patch. It is provided in another embodiment that the adhesive strip is disposed on the foam patch, preferably on the proximal side, preferably close to an edge of the foam patch, preferably substantially adjoining an edge of the foam patch, more preferably extending to a lateral and/or longitudinal edge of the foam patch. In another design, the adhesive strip has an annular design. In a preferred design, the adhesive strip is designed as a ring, substantially have an exterior shape corresponding to the exterior shape of the foam patch. It is provided in another design that the adhesive strip is, at least in part, wider than the rest of the adhesive strip, superior to the tracheostoma, or the air-impermeable region, respectively. It is provided in another embodiment that the adhesive strip comprises the shape of a ring segment. It is provided in another design that an adhesive strip, in addition to, or alternatively to, further adhesive strips, can be attached inferior to the tracheostoma.

Lastly, a use of a tracheostoma protection as described above is proposed for selective airtight closure of a tracheostoma. The tracheostoma protection can also be used to humidify and/or warm the inhaled air. It is likewise provided in accordance with one design, that the tracheostoma protection is provided in order to prevent ingress of foreign matter in the trachea.

Further advantageous designs can be derived from the following drawings. The developments depicted therein are not, however, to be interpreted as limiting, but rather, the features described therein can be combined with one another and with the features described above to form further designs. Moreover, it should be noted that the reference symbols in the descriptions of the Figures do not limit the scope of protection for the present invention, but refer only to the exemplary embodiments illustrated in the Figures. Identical parts or parts having identical functions have the same reference symbols. Therein:

DETAILED DESCRIPTION OF THE PREFERRED EMBODIMENTS

Figure 1:
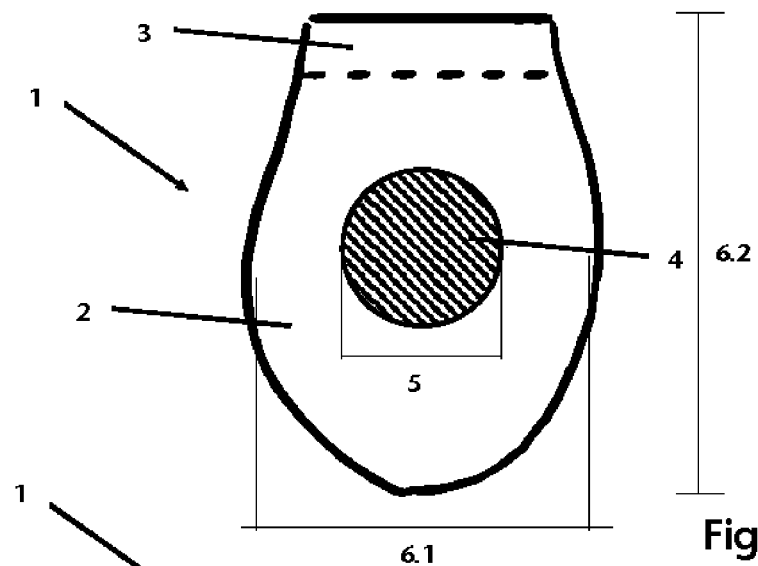
FIG. 1 shows a tracheostoma protection in a top view, from the distal side.

FIG. 1 shows a tracheostoma protection device 1 in a top view, from the distal side. The tracheostoma protection device comprises a foam patch 2 as well as an adhesive strip 3 indicated in FIG. 1, which is disposed on the proximal side of the foam patch 2. Furthermore, the tracheostoma protection 1 has an air-impermeable region 4, preferably in the form of a button. The diameter 5 of the button is approx. half as large as the transverse diameter 6.1 of the foam patch 2 in the illustrated embodiment. The longitudinal diameter 6.2 of the foam patch 2 is also twice as large, or more than twice as large as the diameter 5 of the button 4.

Figure 2:
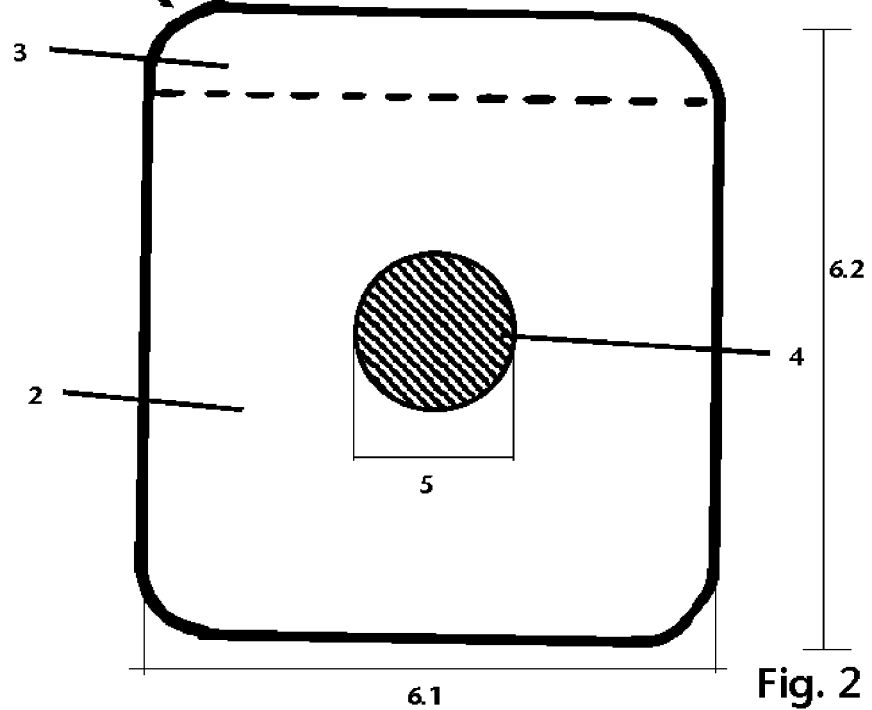
FIG. 2 shows another design of a tracheostoma protection from the same perspective.

FIG. 2 shows another design of the tracheostoma protection device 1, which likewise has a foam patch 2, an adhesive strip 3 on the proximal side of the foam patch 2, and an air-impermeable region 4 on the distal side of the foam patch 2. In the illustrated design, the diameter 5 of the air-impermeable region 4 is substantially smaller than the transverse diameter 6.1 and the longitudinal diameter 6.2, in particular approx. one third thereof.

Figure 3:
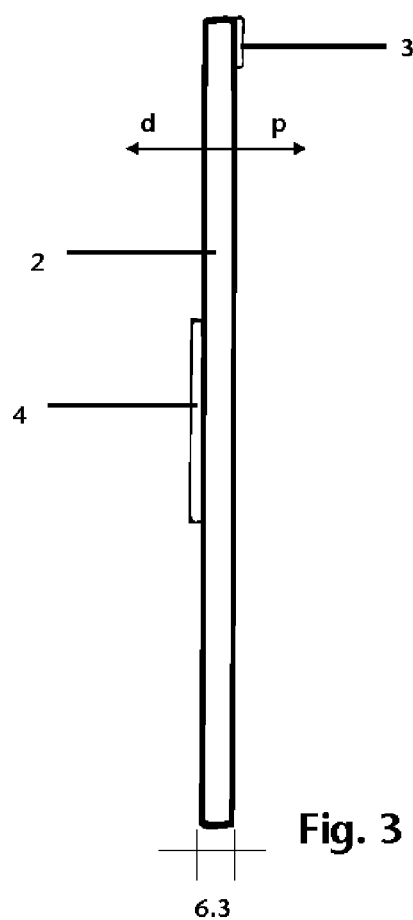
FIG. 3 shows a side view of a tracheostoma protection.

FIG. 3 shows a tracheostoma protection device 1 in a side view. In the side view, it can be clearly seen that the button 4 is disposed on the distal side d, in particular glued thereto. An adhesive strip 3 is applied to the proximal side p, in particular designed as a double-sided adhesive tape. It can furthermore be seen that the foam patch 2 exhibits a relatively small thickness 6.3 of approx. 2 mm to approx. 5 mm.

Figure 4:
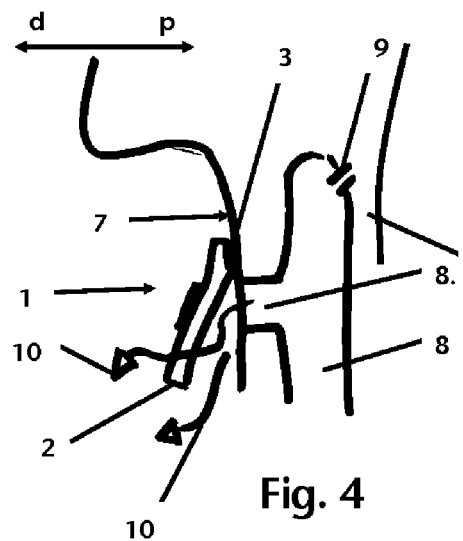
FIG. 4 shows, schematically, the functionality of the tracheostoma protection.

FIG. 4 shows a simplified, schematic illustration of the use of the tracheostoma protection device 1. The tracheostoma protection 1 is disposed on the throat 7 of a user or patient by means of the adhesive strip 3. During exhalation, an airflow 10 flows from the trachea through the tracheostoma 8.1. The tracheostoma protection 1 is lifted away from the throat as a result, such that the airflow 10 can flow, at least in part, past the tracheostoma protection device 1. A portion of the airflow 10 continues to flow through the foam patch 2 and warms and moisturizes it.

Figure 5:
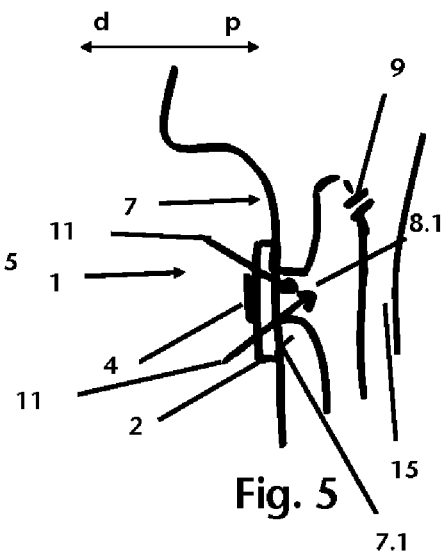
FIG. 5 shows, schematically, the functioning of the tracheostoma protection during inhalation.

FIG. 5 shows the same situation shown in FIG. 4, wherein the user inhales. The airflow 11 during inhalation flows through the foam patch 2, wherein the foam patch 2 lies against the throat 7 of the patient thereby, and in particular, fits against a contact plane 7.1 of the throat. Even when the air-impermeable region 4, formed as a button in this design, covers the region of the tracheostoma 8.1, the dimensions of the foam patch 2, or its thickness, are such that the airflow 11 can readily or easily flow past the air-impermeable region 4. A sealing is thus only generated when the user presses on the air-impermeable region 4.

Figure 6:
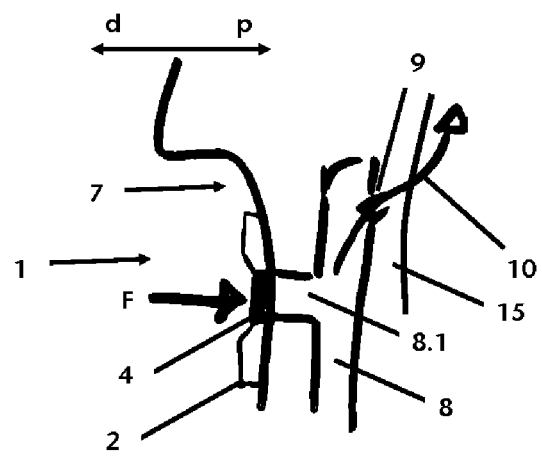
FIG. 6 shows, schematically, the functionality of the tracheostoma protection during initiation of the speech process.

FIG. 6 shows the tracheostoma protection device 1 on the throat 7 of the patient, wherein a force F, exerted by a finger, for example, acts on the air-impermeable region 4. By exerting the force, the foam patch 2 is compressed in the region of the tracheostoma 8.1, such that the exhaled air 10 cannot escape through the tracheostoma 8.1. Instead, the airflow 10 flows through a voice prosthesis 9, which connects the trachea 8 to an esophagus 15. In this manner, the user or patient is able to speak.

The invention claimed is:

1. A tracheostoma protection device for covering a tracheostoma, comprising; an open-cell foam patch, an adhesive strip and an air-impermeable region fixed directly to the foam patch and configured to be allocated to the tracheostoma, wherein the air-impermeable region is configured to cover the tracheostoma and wherein the foam patch is adapted to be moved distally, at least partially, away from a contact surface during use of the tracheostoma protection device.

2. The tracheostoma protection device according to claim 1, characterized in that an airflow flows substantially through the foam patch during inhalation when the tracheostoma protection device is in use.

3. The tracheostoma protection device according to claim 1, characterized in that an airflow flows at least in part past the foam patch during exhalation when the tracheostoma protection device is in use.

4. The tracheostoma protection device according to claim 1, characterized in that the foam patch has a transverse and/or longitudinal diameter that is at least twice as large as a diameter of the air-impermeable region.

5. The tracheostoma protection device according to claim 1, characterized in that the foam patch has a thickness of approximately 1 mm to approximately 6 mm.

6. The tracheostoma protection device according to claim 1, characterized in that the air-impermeable region comprises a button, a plate and/or a skin of the foam patch.

7. The tracheostoma protection device according to claim 6, characterized in that the button, the plate and/or the skin are glued, welded and/or sewn on.

8. The tracheostoma protection device according to claim 1, characterized in that the air-impermeable region can be moved proximally during use, in order to initiate a speech function.

9. The tracheostoma protection device according to claim 1, characterized in that the tracheostoma can be closed by means of the air-impermeable region.

10. The tracheostoma protection device according to claim 1, characterized in that the adhesive strip is disposed on the foam patch such that it can be attached substantially superior to the tracheostoma.

11. A method of using a tracheostoma protection device for covering a tracheostoma comprising the steps of: forming an open-cell foam patch, an adhesive strip, and an air impermeable region fixed directly on the foam patch and allocated to the tracheostoma; covering the tracheostoma with the air impermeable region; moving the foam patch at least partially away from a contact surface during use of the tracheostoma protection device; and positioning the foam patch for selective sealing of the tracheostoma.

* * * * *